United States Patent
Hope

(10) Patent No.: US 12,285,292 B2
(45) Date of Patent: Apr. 29, 2025

(54) ULTRASONIC INSPECTION OF COMPLEX SURFACES

(71) Applicant: DarkVision Technologies Inc., North Vancouver (CA)

(72) Inventor: Jay Roderick Hope, Vancouver (CA)

(73) Assignee: DarkVision Technologies Inc., North Vancouver (CA)

( * ) Notice: Subject to any disclaimer, the term of this patent is extended or adjusted under 35 U.S.C. 154(b) by 292 days.

(21) Appl. No.: 17/960,820

(22) Filed: Oct. 6, 2022

(65) Prior Publication Data
US 2023/0130123 A1    Apr. 27, 2023

(30) Foreign Application Priority Data
Oct. 21, 2021   (GB) .................................... 2115164

(51) Int. Cl.
   *A61B 8/00*    (2006.01)
   *G01S 15/89*    (2006.01)
(52) U.S. Cl.
   CPC ........ *A61B 8/4483* (2013.01); *G01S 15/8915* (2013.01)
(58) Field of Classification Search
   USPC ......................................................... 73/627
   See application file for complete search history.

(56) References Cited

U.S. PATENT DOCUMENTS

| | | | | |
|---|---|---|---|---|
| 3,186,216 A | * | 6/1965 | Dickinson, III | ....... B23Q 17/09 |
| | | | | 73/627 |
| 3,250,120 A | * | 5/1966 | Dickinson, III | ..... G01N 29/043 |
| | | | | 73/600 |
| 2014/0283611 A1 | * | 9/2014 | Habermehl | .......... G10K 11/346 |
| | | | | 73/602 |
| 2021/0103052 A1 | * | 4/2021 | Rae | ......................... G01S 7/539 |
| 2021/0239652 A1 | * | 8/2021 | Baelde | ................. G01N 29/043 |

FOREIGN PATENT DOCUMENTS

| | | | | |
|---|---|---|---|---|
| CN | 104936517 A | * | 9/2015 | ........... A61B 8/0841 |
| CN | 110772281 A | * | 2/2020 | ........... A61B 8/0825 |
| GB | 2588102 A |   | 4/2021 | |

OTHER PUBLICATIONS

Mao, Q., et al., "A Fast Interface Reconstruction Method for Frequency-Domain Synthetic Aperture Focusing Technique Imaging of Two-Layered Systems with Non-planar Interface Based on Virtual Points Measuring", Journal of nondestructive evaluation, vol. 39, 2020, pp. 1-10.

Search Report received for GB Apllication No. 2115164.2, mailed on Jul. 1, 2022, 2 pages.

* cited by examiner

*Primary Examiner* — Clayton E. LaBalle
*Assistant Examiner* — Warren K Fenwick

(57) ABSTRACT

A device and method used to log images of target objects with ultrasound transducers. The object may be a fluid-carrying tubular, such as a pipeline. The transducers operate as phased arrays, insonifying areas of the target object with a plane wave and then storing the reflected signals. The signals are sampled and summed for each pixel, by considering various paths taken by the wave from transmitting to receiving via that pixel. Refraction and reflection from surfaces are used to determine segments of the paths.

22 Claims, 12 Drawing Sheets

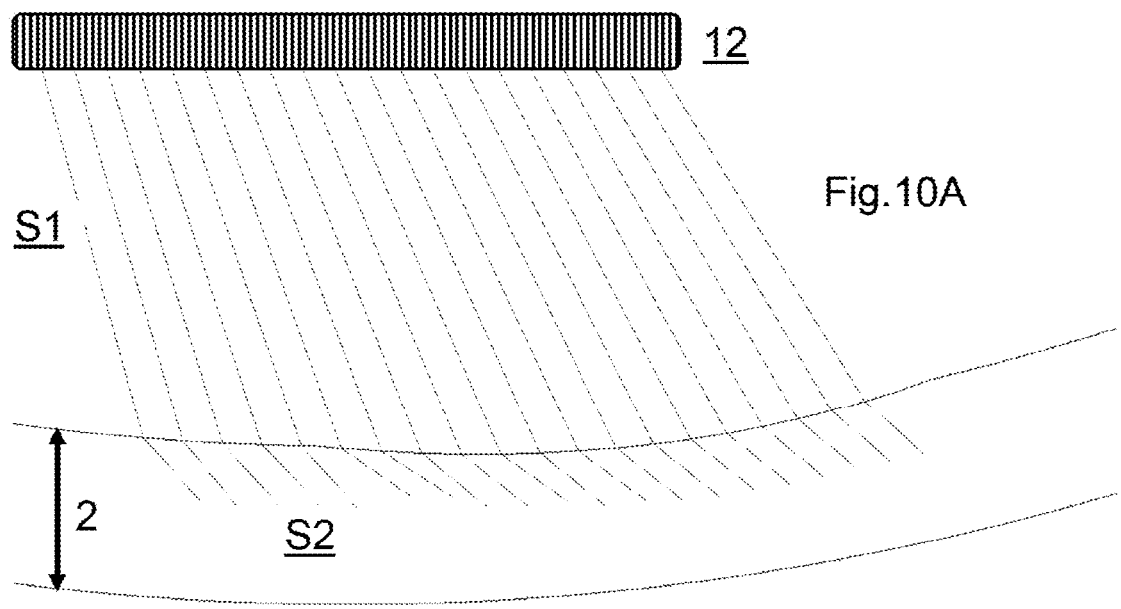
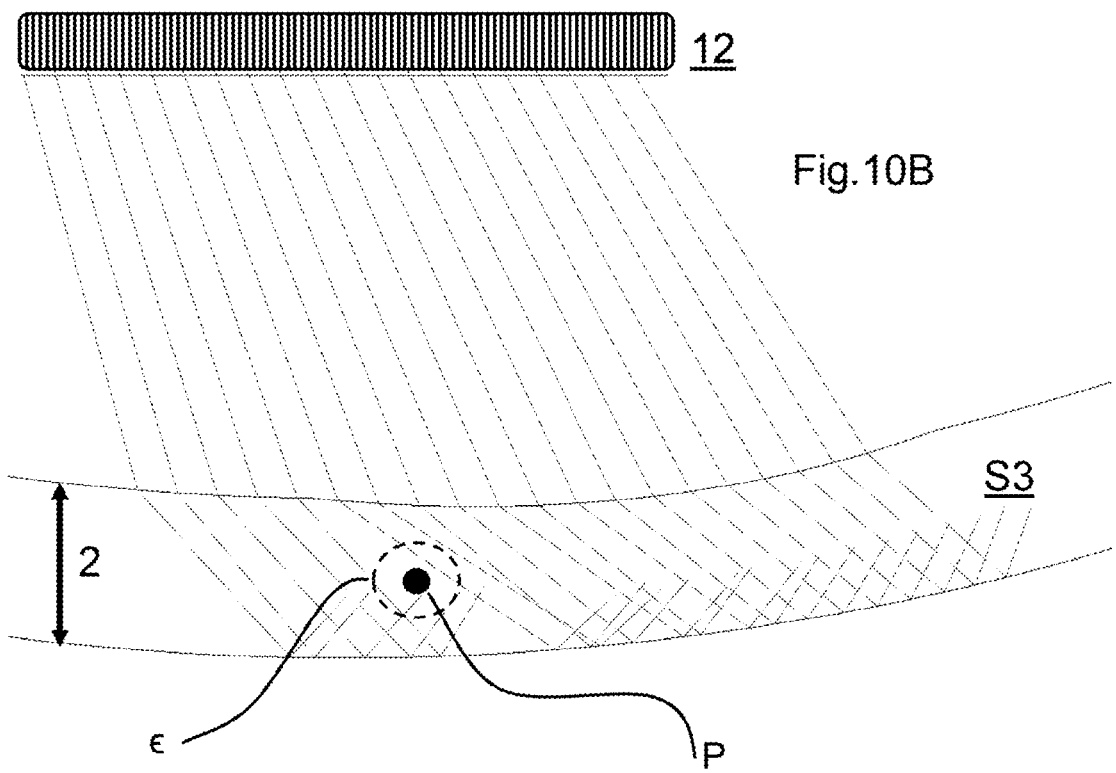
Fig.13

ULTRASONIC INSPECTION OF COMPLEX SURFACES

RELATED APPLICATIONS

This application claims priority to GB Application No. 2115164.2, filed on Oct. 21, 2021, which is incorporated herein by reference in its entirety.

FIELD

The invention relates generally to inspection of complex parts and tubulars by ultrasound, in particular Non-Destructive Testing, wellbore inspection and In Line Inspection of pipelines for defects.

BACKGROUND OF THE INVENTION

Ultrasound is commonly used for Non-Destructive Testing (NDT) of parts and logging long fluid-carrying tubulars/conduits for defects such as cracks and voids. In wells and fluid carrying pipes, such as oil wells, pipelines, and water delivery infrastructure, there often arises a need to inspect the internal structure for integrity or obstructions. For example, hydrocarbons in production casing may contaminate ground water if there are cracks or deformations in the casing. Similarly, water resources may be lost to leaks in water mains. Ultrasound sensors are a known way of imaging such structures to detect problems thus protecting the environment.

In phased array systems, as shown in FIG. 1, an aperture of several acoustic elements receives delayed electrical pulses to transmit a focused wave 8, generally perpendicular to a surface of the tubular, as a scan line and then proceeds to the next scan lines to create a frame. The image is thus built up of direct reflections from the insonified spot and behind. The scan line will actually bounce around the tubular and return stray reflections, but these are either filtered out or form part of the noise attributed to the location of each insonified spot.

Typically, ultrasound inspection tools are deployed into the tubular and image the surface as they move axially therethrough. In various commercial products, an ultrasonic transducer emits a wave towards the part then reflects off defects and boundary layers back towards a receiving transducer. The receiver and transmitter may be the same in pitch-echo designs or separated in pitch-catch designs. The time of flight (ToF) of the ultrasonic wave is measured and, knowing the speed of sound in the part, a distance to those reflectors is calculated. This is repeated for many locations or using many transducers to build up a geometry of the whole part. Defects such as cracks and voids disrupt the wavefront and tend to show up as glints or shadows in the returned signal that cannot be attributed to the contours of the part. FIG. 5 provides an illustration of cracks 27, rusty surfaces 23, and voids 28 in a tubular 2.

The wave typically travels through a coupling fluid 13, which either has a predictable or no effect on the path, allowing the computation to consider only the defects and surfaces as reflectors. The surface of the part or tubular is preferably flat or normal to the transducer to simplify the geometry and path calculation.

A problem arises when the surface of the part is uneven, complex or unknown, worse still when the transducers are an unknown standoff distance from the part thru a medium of unknown Speed-of-Sound. Eccentricity of the tool, irregularities in logging movement, and mixed fluid environments tend to lead to such situations. There are then too many unknows to solve the path uniquely. The real reflections from these multipaths instead show up as noise in the final image.

SUMMARY OF THE INVENTION

In accordance with a first aspect of the invention there is a method of imaging a tubular comprising: transmitting a wave towards the tubular using a phased-array ultrasound transducer; storing received reflection signals reflected off the tubular in a data store; performing receive beamforming on the reflection signals to locate an inner surface of the tubular; defining an inner-surface boundary model, using the located inner surface; tracing rays from the transducer through locations within the tubular and back to the transducer, using the inner-surface boundary model and incorporating localized refractions; calculating a Time of Flight (ToF) for the rays using a speed of sound (SoS) of a coupling fluid and of the tubular; and using the ToF, sampling and summing the stored reflection signals to calculate image values for pixels representing the tubular; and assembling the pixels to visualize the tubular.

In accordance with a second aspect of the invention there is an imaging system for imaging a tubular comprising: an imaging tool disposable in the tubular; an ultrasound phased-array radially distributed around a body of the tool; drive circuits operatively coupled to the array and programmed to transmit a wave; a memory for storing received reflection signals from the array. There are processing circuits programmed to: perform receive beamforming on the reflection signals (raw or compressed via demodulation) to locate an inner surface of the tubular; define an inner-surface boundary model from the located inner surface; trace rays from the transducer through locations within the tubular and back to the transducer, using the inner-surface boundary model and incorporating localized refractions; calculate a Time of Flight (ToF) for the rays using a speed of sound (SoS) of a coupling fluid and of the tubular; and using the ToF, sample and sum the reflection signals to calculate image values for pixels representing the tubular; and assemble the pixels to visualize the tubular.

The aspects may repeatedly measure and record the speed of sound of the coupling fluid, wherein said calculating the ToF includes using a recorded speed of sound measurement corresponding to a closest location to be visualized The aspects may define an outer-surface boundary model for an outer surface of the tubular, for calculating reflections in the traced rays off the outer surface.

Rays may be traced and stored in a memory and then retrieved based on closeness to a given pixel to calculate the pixel's image value. There may be plural rays selected for each location in the tubular and at least some of the plural rays terminate at multiple transducer elements.

The reflection signals may be stored in RF or demodulated form. The image values may be demodulated brightness values. The method may interpolate image values for pixels between pixels that have image values.

The method may transmit a plurality of additional waves, each transmitted at a different steering angle and compounding the image values from each of the transmitted waves The inner surface may be located using a first steering angle normal to the tubular surface and wherein the rays are traced from a second steering angle not normal to the tubular surface.

The wave may be transmitted to contact the inner surface at a constant incidence angle. The transmitted wave may be a defocused wave or diverge away from the transducers. The wave may have a curved wavefront.

The inner-surface boundary model may be a set of pixel coordinates, or a mathematical equation fit through the located inner surface.

The ultrasound transducer elements used for transmitting the wave may be the same or different for receiving reflections of that wave.

The phased-array may be divided into plural array segments. Each segment may transmit waves and receive reflections, separate from the other segments. Each segment may image a separate region of the tubular. The regions may partly overlap.

The processing circuitry may be located remote from the tool and receives the reflection signals from the memory located on the tool.

There may be a speed of sound sensor and the memory may be arranged to store a speed of sound log from said sensor.

BRIEF DESCRIPTION OF THE DRAWINGS

Various objects, features and advantages of the invention will be apparent from the following description of embodiments of the invention, as illustrated in the accompanying drawings. The drawings are not necessarily to scale, emphasis instead being placed upon illustrating the principles of various embodiments of the invention.

FIG. 10A is an illustration of rays passing through a tubular

FIG. 10B is an illustration of rays passing through a tubular, including a reflection off the outer surface.

DETAILED DESCRIPTION OF THE PREFERRED EMBODIMENTS

With reference to the accompanying figures, devices and methods are disclosed for capturing, processing, and storing ultrasound reflections from a target object by an ultrasound phased array transducer. The target object may be a tubular such as a water pipeline, oil & gas pipeline, or downhole casing. An imaging tool carries ultrasound transducers that transmit acoustic waves to the surface and receives the reflections from the inner surface, outer surface, and defects within the object. The processing reconstructs an image of the object by considering various paths that the ultrasound energy could have taken from any given point to the transducer elements.

Figure 7:
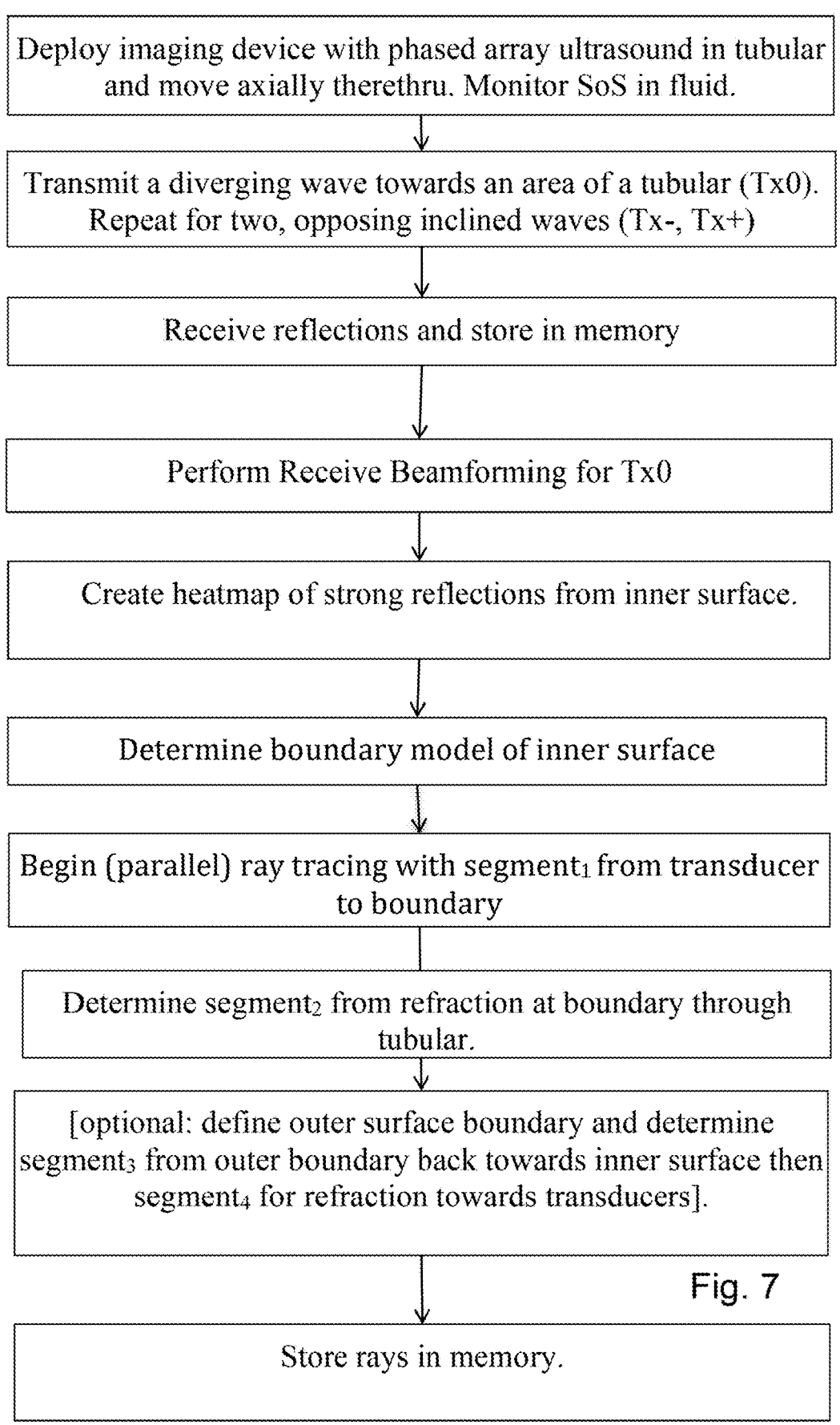
FIG. 7 is a flowchart for tracing rays.

FIG. 7 illustrates a workflow for processing the ultrasound reflection data for the use case of a fluid-carrying tubular, as detailed below. In brief terms, the process comprises insonifying the tubular with plane waves; defining a boundary between fluid 13 and the tubular's inner surface; tracing acoustic rays from transducer through the tubular; and then sampling and summing signals for transducers that are the terminus along rays from each pixel.

Figure 12:
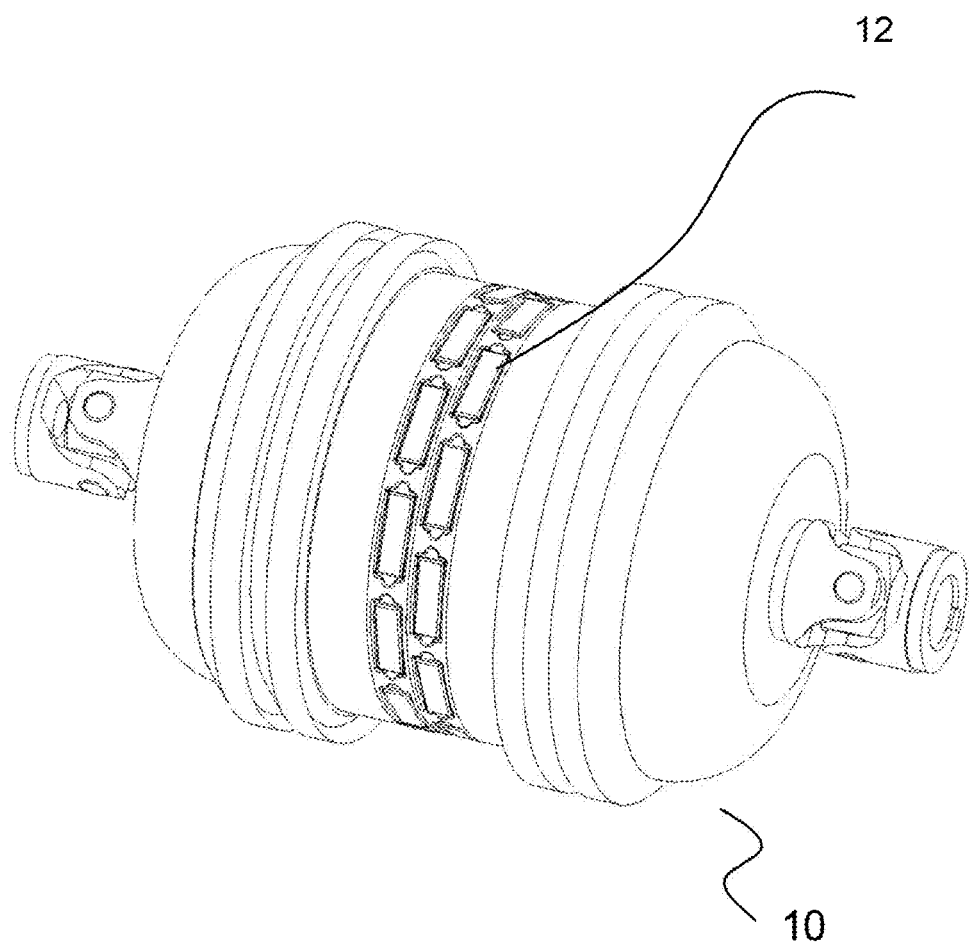
FIG. 12 is a perspective view of an imaging tool for a pipeline.

The imaging tool is typically placed in the tubular and moved axially through it using wireline, coiled tubing, tractoring or fluid pressure. As shown in FIG. 12, an imaging tool 10, such as an In Line Inspection tool (aka PIG), has a large array of transducers 12 radially disposed around the housing of the tool, facing generally outwards towards the tubular. The array may be broken down into several array segments, physically separated from each other. Several parameters are known or measurable, such as diameter of the tubular, standoff distance to the inner surface, thickness of tubular, Speed of Sound in the fluid and in the tubular.

The imaging tool may be moving very quickly through the tubular, so the imaging is preferably performed by transmitting wide waves towards the tubular, storing the reflection in raw form and then post-processing the reflections to render an image of the tubular.

For the sake of logging speed, the transmit wave is transmitted by many transducer elements as a wavefront to insonify a large arc of the tubular, most efficiently insonifying the whole 360° cross-section during each transmit event. This wave can take a variety of different forms, including flat, arcuate, angled (steered), virtual point source, polar angled, and others. Arcuate waves can be seen as the polar coordinate equivalent of flat waves in rectangular coordinates. These shapes are created by phase delays set in the FPGA and computed by the onboard CPU from each element in the phased array such that a coherent wave front is produced. Notably, these waves do not converge or focus at the inner surface 20. After the transmit event, the transducers in the phased array are electronically switched into a receive state where ultrasonic reflection are converted to electrical data signals. These signals can be stored for future post processing of the data, or they can be processed in real time on the device. The received ultrasound energy will therefore include many confounding reflections from plural reflectors and plural paths. These may be sorted out in post processing.

The processor may be remote from the imaging tool and comprise a memory, CPUs, GPUs and instructions for carrying out the disclosed method. The processor may use an NVIDIA OptiX Ray-Tracing engine, designed for highly efficient parallel processing of light rays for video games and repurposed herein for wave paths.

The image is resolved using a receive beamforming algorithm on the captured data. The favorable approach is to use delay and sum, in which spatial coordinates are converted to a set of delays that are used to sample the channel data. The delays are calculated by determining the return trip distance for the plane wave to reach a given coordinate, then reflect back to each element in the phased array. The distance values are converted to time delay values by dividing the distances of each segment in the ray by the speed of sound of the two media. The delays are then used to sample the RF channel data for each element at the terminus of the valid rays. Then the values of the samples are added. The magnitude of combined signals is then converted to an intensity value for the given pixel. This calculation is performed for every pixel in the ultrasound image. This approach amplifies any scatterers that may be present at every pixel location.

Figure 9A:
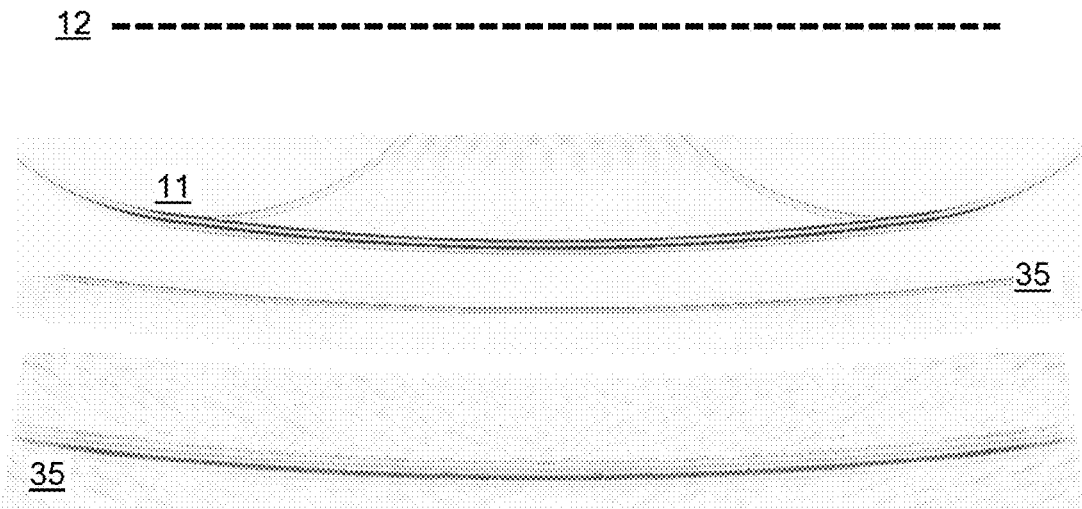
FIG. 9A is an image of a heat map of inner and outer surface reflections.

The processor determines a definition of the inner surface of the tubular at some distance away from the transducers using the first, large reflection per element, i.e. a reflection above some threshold energy within some initial time window, given the speed of sound of the fluid and expected standoff to the tubular. Alternatively, the initial result may be a heat map 35 of the brightest reflections around the surface (see FIG. 9A), through which an edge is computed, and a boundary is defined through this edge. For this, the processor may use edge detection algorithms common in image processing, such as Sobel filters, particularly optimized for edges normal to the direction of the wave. Alternative methods of finding and modeling the surface include Convolutional Neural Nets or the method taught in Patent Application GB1914401.3 filed 4 Oct. 2019 entitled "Surface Extraction for Ultrasonic Images Using Path Energy."

A numeric model of the boundary 25 of the tubular is computed from the beamformed image above. Several methods can be employed to achieve this result. The resulting model is a continuous curve that traces points of the image where the boundary is computed. This information can be used for subsequent Rx beamforming algorithms.

Figure 9B:
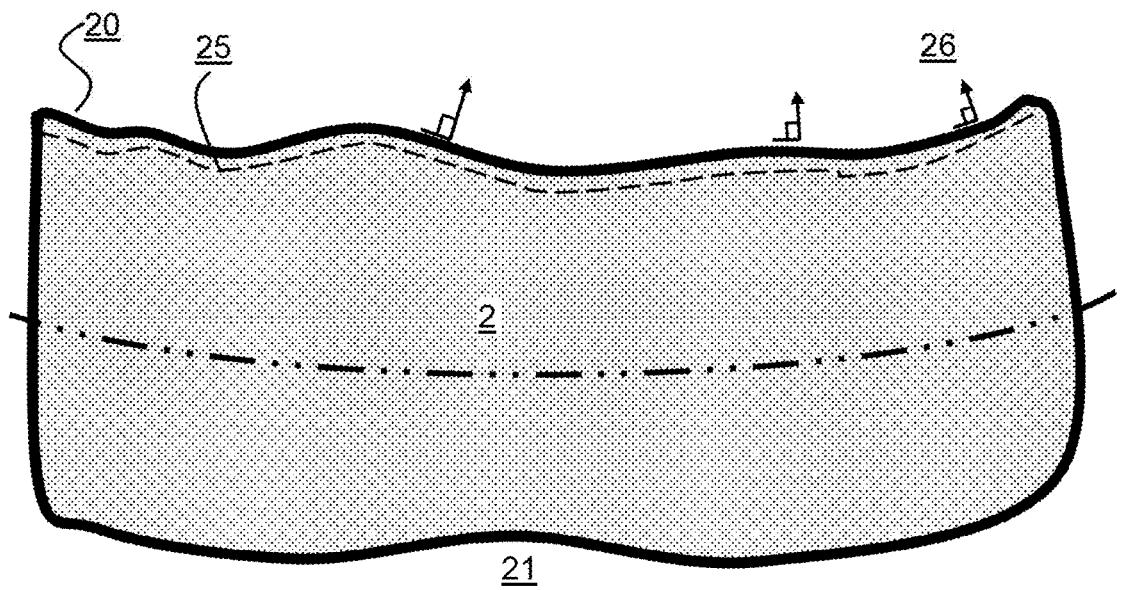
FIG. 9B is an illustration of contours fitted through surfaces of a tubular

This boundary 25 can be represented and stored as a set of points $\{R1, \vartheta1, R2, \vartheta2, R3, \vartheta3, R4, \vartheta4, R5, \vartheta5 \ldots Rn, \vartheta n\}$ or mathematical equation $R=F(\vartheta)$ fit through the points, e.g. spline, line, polynomial or trigonometric functions. FIG. 9B shows an excessively deformed surfaces 20, 21, boundary fit 25 (dashed), and surface normals 26. This surface representation is more precise than the assumed circular tubular and encodes warping, eccentricity, dents, and other defects from a true circle. A derivative can be applied to the model to infer the surface normal direction vector 26 for every point along the curve. The surface representation is used to determine the point where a sound wave refracts into the metal using Snell's Law and localized contour. So, although the transmitted wave was created to provide some assumed angle of incidence and refraction angle into the tubular, there will be deviations from this based on the actual localized contours of the surface.

Additionally, the processing steps may include a second surface definition, this time for the outer surface of the tubular. This is included in the modelling or reflection from the outer surface and back along path segments S3 to the transducer.

As shown in FIG. 10A, the refraction paths along the surface differ depending on the localized contour of the boundary. The localized contour at a given point along the surface may be computed as a line joining two (or more) nearby points from the boundary definition or from the slope of the fitted line.

In order to receive beamform beyond the boundary (i.e. inside the tubular), the model of the tubular boundary is taken into account to determine the delays used for the delay and sum beamforming method. The delays are computed using a ray tracing algorithm. The processor calculates a set of transmitted rays (from transducer elements into the tubular) and reflection rays (from tubular to transducer elements). For each pixel, the total time for transmission and reflection is added.

The transmitted wave is represented as a number of rays, that are drawn perpendicular to the wave front 11, as it propagates through the fluid. This provides a method of determining the path length of the transmitted wave to a given spatial position. The intersecting points on the boundary model for the rays are computed, along with the corresponding surface normal vector of each intersection point. For each ray, the angle between the ray and the corresponding surface normal 26 is calculated. Then, the refracted ray vector is computed by using Snell's Law. After this computation is completed, for every ray, there is now a second segment S2 within the tubular. These rays travel at the speed of sound of the tubular solid, which can be the shear wave velocity or the longitudinal wave velocity.

Thus the first segment in each acoustic ray is the direct transmit path segment S1 from the transducer element to the inner surface and the second segment is the refracted path into the tubular S2. As shown in FIG. 10B, the processor may proceed to calculate further path segments S3 reflecting off the outer surface of the tubular, and segments S4 (not shown) refracting back to the fluid-tubular interface. At some point, the energy in the segments diminish to some level that can be ignored. Each ray segment can be defined by starting coordinate (x,y) and vector (i, j). The system may store each ray in memory as a list of segments.

E.g. Ray={S1(x1,y1, i1,j1); S2(x2,y2, i2,j2); S3(x3,y3, i3,j3); S4(x4,y4, i4,j4)}

As exemplified by FIGS. 10A, 10B although the transmitted rays start parallel, some of them converge, diverge or cross each other due to the irregular surface. Thus defects within the tubular (e.g. at pixel P) may return reflections via multiple rays that are within distance E of that point P. The signals from these rays can be sampled from multiple transducers that are not necessarily neighbours in the array. Reflection rays may be traced for each transducer element. Because the transducers, in receive mode, are capable of detecting waves over a wide angle, plural reflection rays may be considered for each element. As before, there are direct and refracted segments in each ray. These reflection rays are stored in memory.

Figure 8:
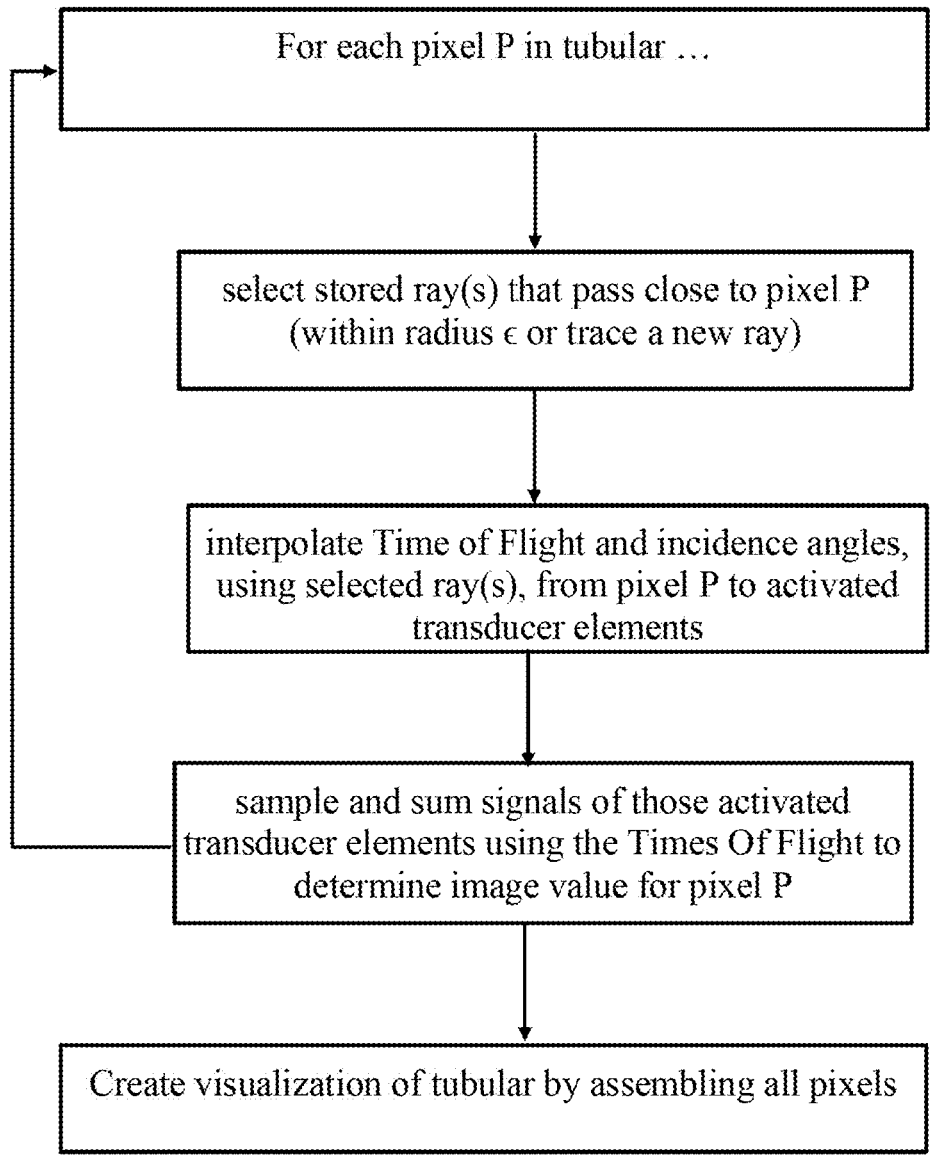
FIG. 8 is a flowchart for imaging using stored rays.

The flowchart of FIG. 8 shows how the processor creates an image for the tubular for pixels (or voxels in 3D images) within the tubular by finding the stored rays closest to each pixel to complete the path from transmission to receive via that pixel. That is, for a given pixel P, the processor determines at least one transmitted ray and at least one reflection ray that passes close to it. The closest ray may be determined as the shortest distance from the pixel along a line that intersects that ray orthogonally. There may be several close rays, which are all included in the calculation, especially if a highly dense transducer array or dense ray set are used.

Using the speed of sound in the tubular and fluid, the processor calculates the time of flights along each selected ray, from transmitter to receiver elements. Only some receiver elements are considered activated for (i.e. relevant to) a given ray. Several neighbouring elements may be assumed to have captured the reflection along a given ray and there are multiple valid rays for each pixel. The remaining receiver elements are not processed for this pixel.

Figure 3A:
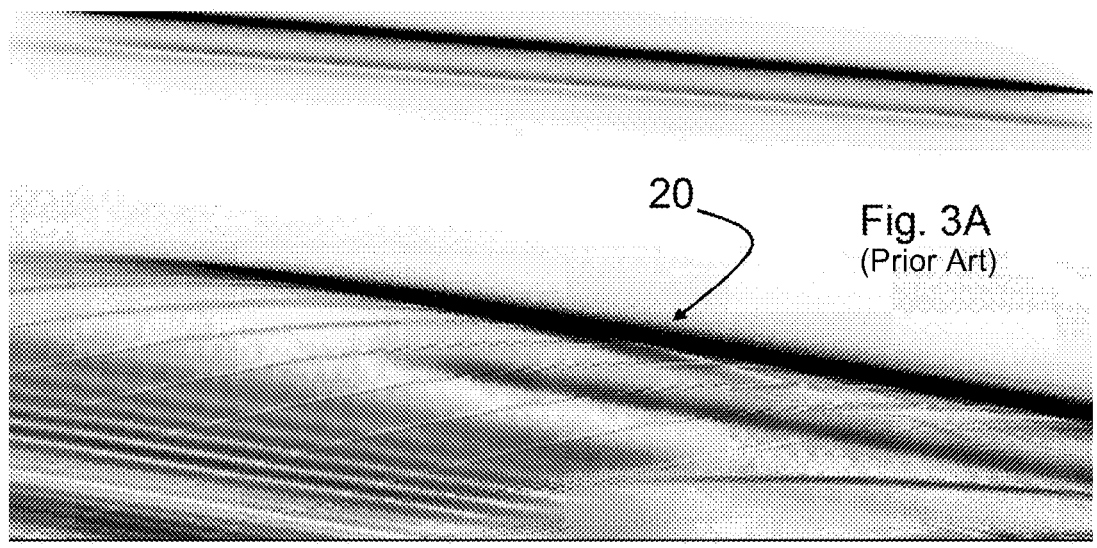
FIG. 3A is a reconstructed image according to prior art methods.
Figure 3B:
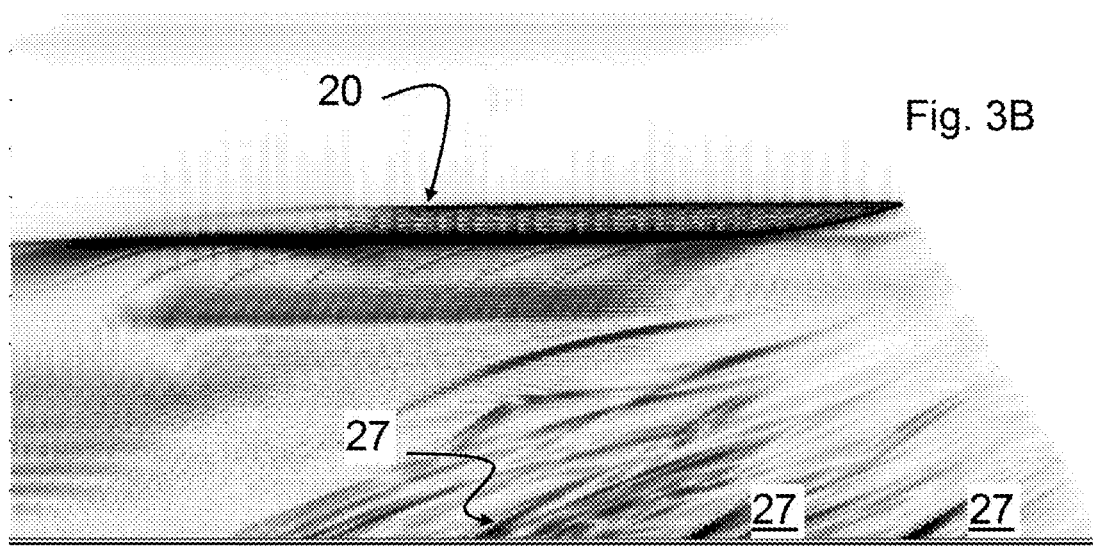
FIG. 3B is a reconstructed image using ray tracing through the inner surface.
Figure 3C:
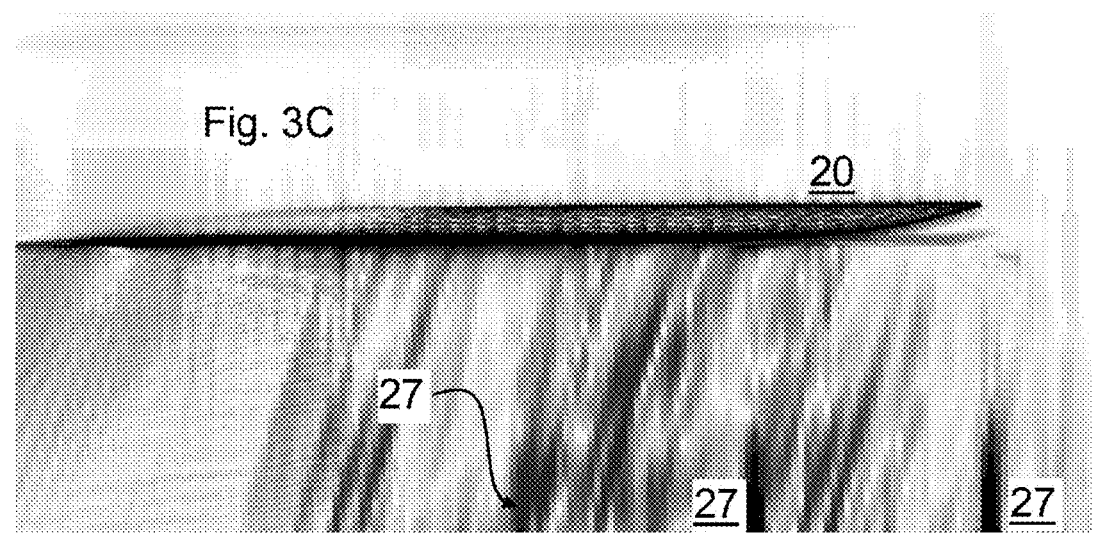
FIG. 3C is a reconstructed image using ray tracing considering the inner and outer surfaces.

The processor then samples the reflection signals for the activated receiver elements using the time(s) of flight and sums the signals to estimate the reflections from that pixel. The summation creates an image value for that pixel, typically expressed as an intensity (i.e. brightness). It is possible that a single receiver element captured reflections from the pixel via multiple paths. Thus a great number of extra transducers are included in the signal summation, compared to direct image processing that results in FIG. 3A. As shown in each reconstructed image of FIGS. 3A, 3B, and 3C, the top is a location near the transducer array, the bottom is the outer surface and the middle is generally near the inner surface 20. In FIG. 3A, the inner surface 20 is visible, but the cracks 27 cannot be seen because their reflections are not coherently summed and so end up looking like noise. 100591 FIG. 3B is a visualization of a tubular 2 with surface 20 and three cracks 27. In this reconstruction, the ray tracing considers only direct transmissions through segments S1, S2 and not reflections off the outer surface provided by segment s3. While this simplifies the calculations, the crack reflections are less bright and are incorrectly shown inclined. In FIG. 3C, the visualization considers the outer surface, which includes more paths to increase the summed intensity and correctly orients the cracks.

Figure 11:
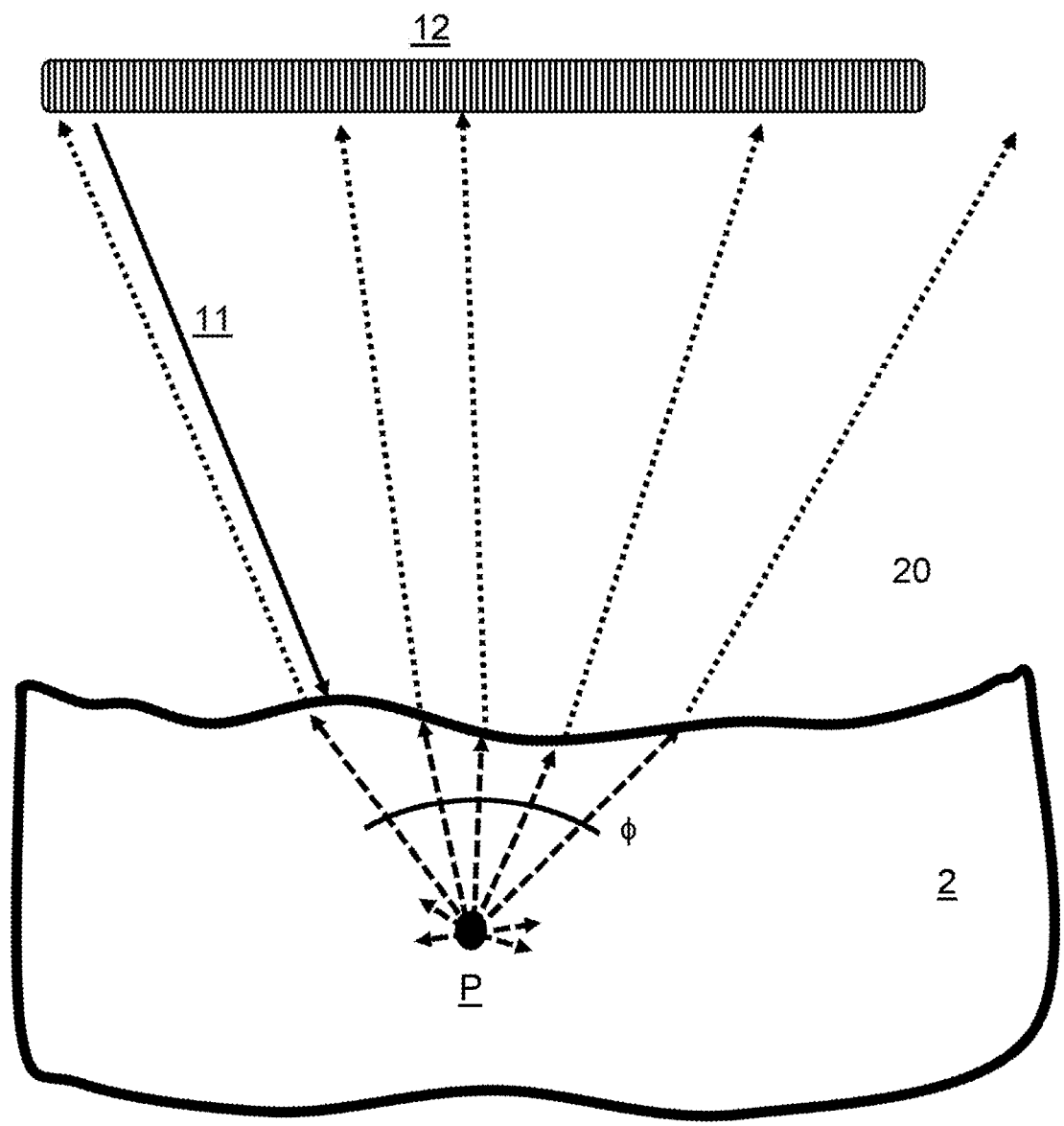
FIG. 11 is an illustration of rays emitting from a pixel back to transducers.

FIG. 11 illustrates how the reflection path from a given pixel P can be calculated by considering the pixel P as an omnidirectional reflector and tracing rays from that pixel back to transducer elements for sampling. As there are no transducers beyond the tubular, the processor may ignore outward-moving waves, unless one considers the weak reflection from the outer surface back towards the transducer 12. Similarly, there will be a range of lateral paths that will not reach the transducer to have been recorded. To speed computation, the processor may consider only rays within a small range of angles facing-inward, that are likely to trace back towards the transducers. The processor may compute multiple rays within the range using parallel processing, optionally implementing a scatter-gun approach to see which rays do trace back to transducers and repeat tracing for rays nearby to those.

The processor may implement a Monte Carlo optimization by randomly selecting ray angles to trace based on some distribution, e.g. tracing more inward rays than sideward rays and fewest outward rays. The complete ray will include reflection segments from P to the transducer elements and transmitted segments from the transducer to P, along the transmitted steered angle. That is, although the pixel P is an omnidirectional reflector it had to have been insonified by the transmitted wavefront. In FIG. 11, only the left-most ray (dashed) is parallel to the transmitted wave 11 but the other rays could be segments in the reflection path.

Figure 4:
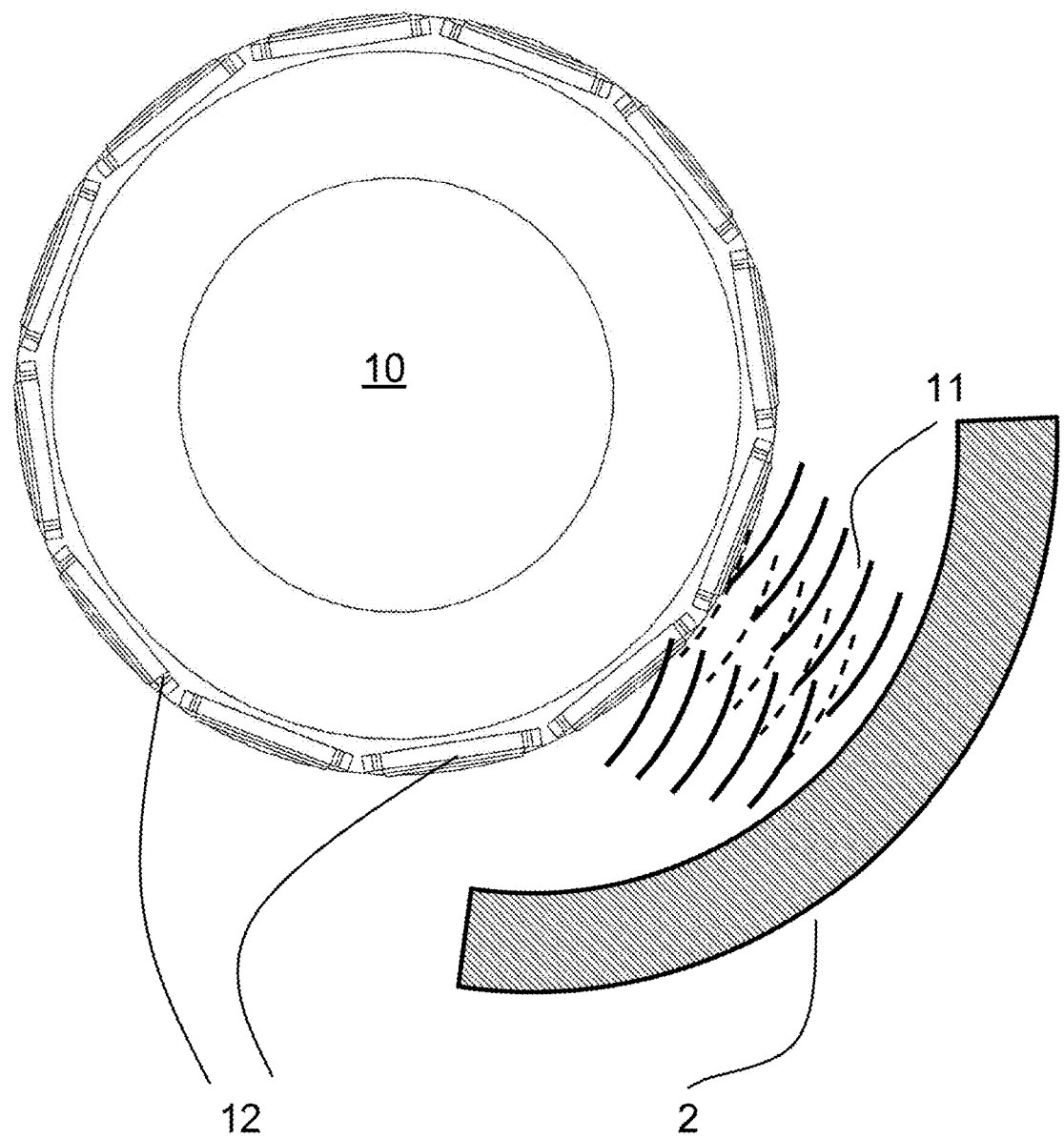
FIG. 4 is a cross-section view of the imaging tool transmitting plane waves from plural angles.
Figure 5:
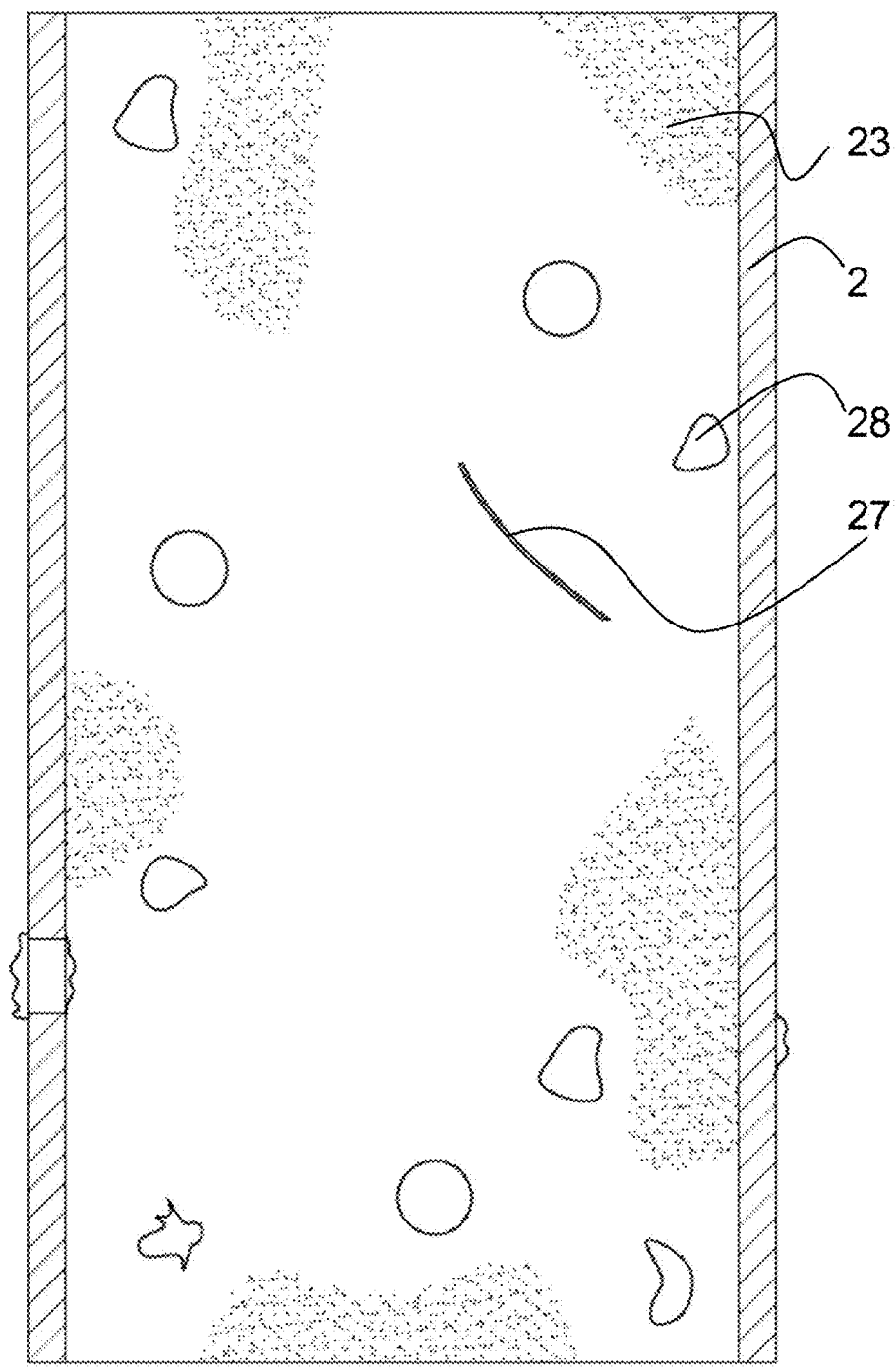
FIG. 5 is a cross-section side view of a damaged tubular.

In the embodiment of FIG. 4, plural plane waves 11 are transmitted at different steering angles towards the tubular sequentially to capture features from different perspectives. Overlapping images of the tubular are combined to make the final image. The combined image will detect more features as the transmitted wavefront is more likely to hit them perpendicularly from at least one of the plural angles. The combined image will also result in reduced speckle pattern, clutter and acoustic artifacts. For example, there may be one transmit that is perpendicular (dashed lines) to the tubular and two waves (solid lines) transmitted at equal and opposite steering angles. The first is ideally suited to measure thickness and pick up the location of the inner surface. The latter waves are optimal for creating shear waves and picking up cracks.

Figure 1:
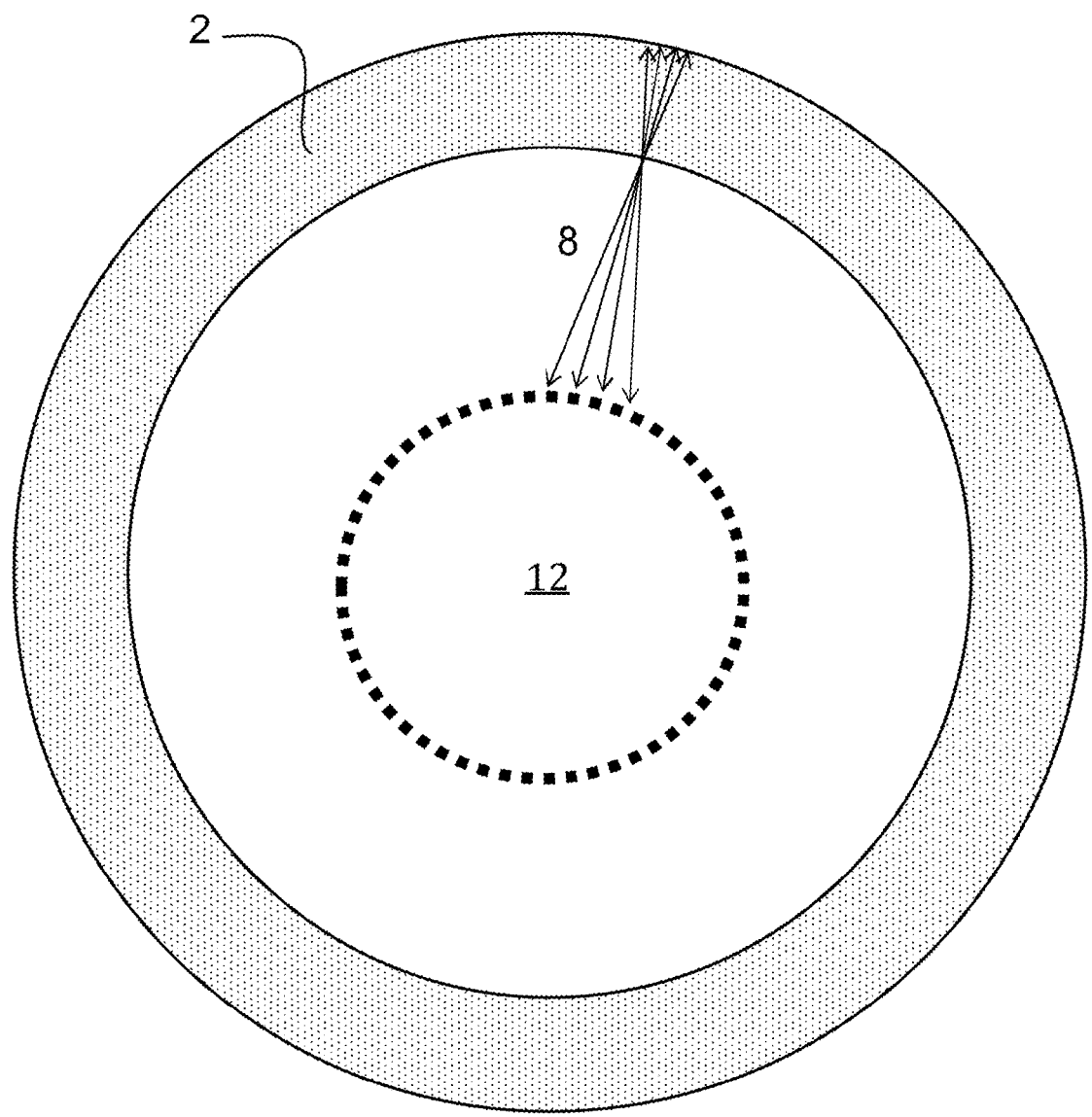
FIG. 1 is end-view of an ultrasound array in a pipe according to a known configuration.
Figure 2A:
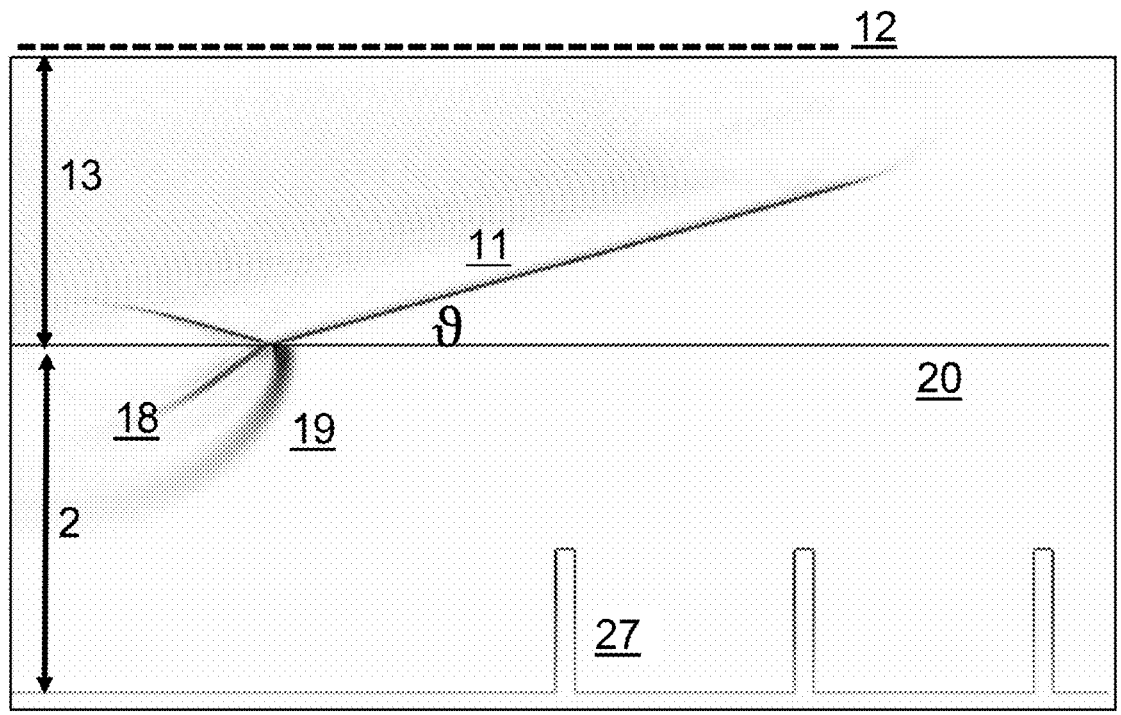
FIG. 2A is a simulated image of a plane wave transmission.

As seen in FIG. 2A, when the wavefront 11 hits the inner surface of the tubular 2, some of the energy penetrates and refracts, assuming the incidence angle is less than the critical angle. The refraction depends on the speed of sound of the fluid and metal, as dictated by Snell's Law. Some portion of this enemy is a shear wave 18 and some is a longitudinal wave 19. In order to return reflections from cracks, it is desirable to have some shear component, as this wave mode and direction is optimal for reflecting off of cracks and back towards the transducer. If the incidence is greater than a second critical, most of the energy will be shear wave. Advantageously, this simplifies image processing of the reflections because addition signals do not have to be considered. Thus, there is a narrow range of incidence angle that is optimal. This is even a more complicated request when logging a curved tubular at high speed.

The simulation of FIG. 2A shows transmitted curved wavefront 11 travelling through fluid 13 towards the tubular 2 and making an instantaneous angle of incidence with respect to the surface. In the metal of the tubular longitudinal wave 19 and shear wave 18 proceed. A suitable angle of incidence 5 is between 16 and 25°, assuming the tubular is steel, and the fluid is water or oil.

Figure 2B:
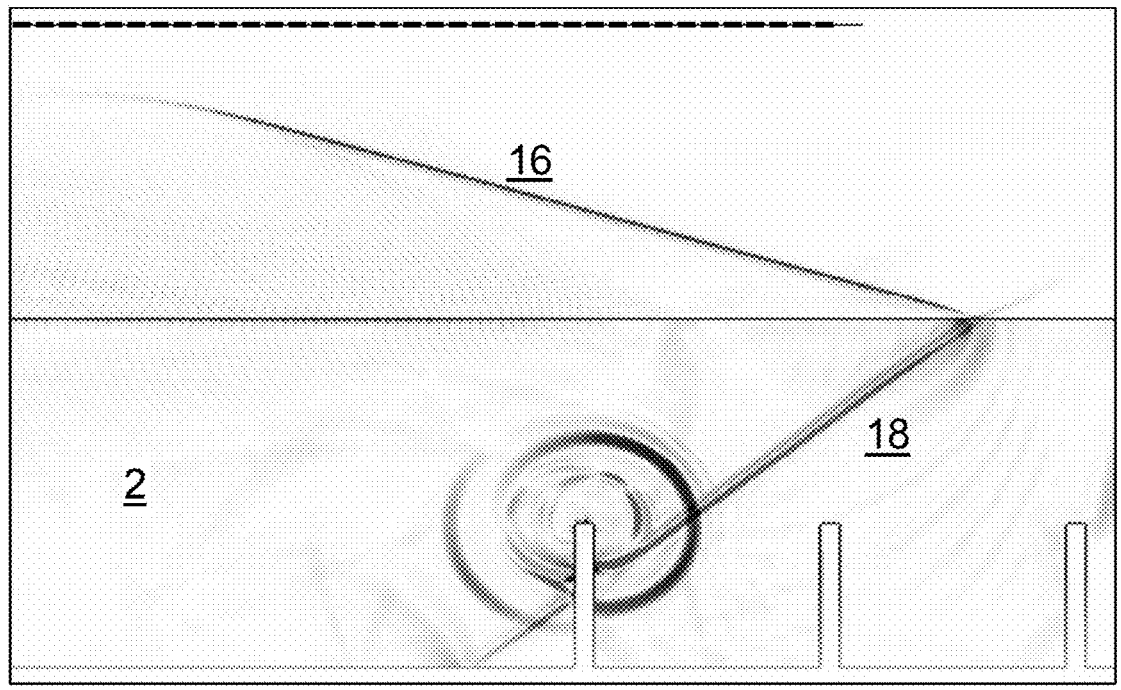
FIG. 2B is simulated image of a plane wavefront entering a target with defects.

As shown in FIG. 2B, the transmitted wavefront continues to insonify the tubular surface at the same angle of incidence. As a result, the shear wave 18 proceeds at the same relative angle within the metal. Note that the wave is defocused at the surface and returns reflections 16 from all features on the surface, while the remaining energy transmits through the surface and reflects off of the outer surface and cracks 27.

The term 'processor' is intended to include computer processors, cloud processors, microcontrollers, firmware, GPUs, FPGAs, and electrical circuits that manipulate analogue or digital signals. While it can be convenient to process data as described herein using software on a general computer, many of the steps could be implemented with purpose-built circuits.

It will be appreciated that the various memories discussed may be implemented as one or more memory units. Non-volatile memory is used to store the compressed data and instructions so that the device can function without continuous power. Volatile memory (RAM and cache) may be used to temporarily hold raw data and intermediate computations.

Figure 6:
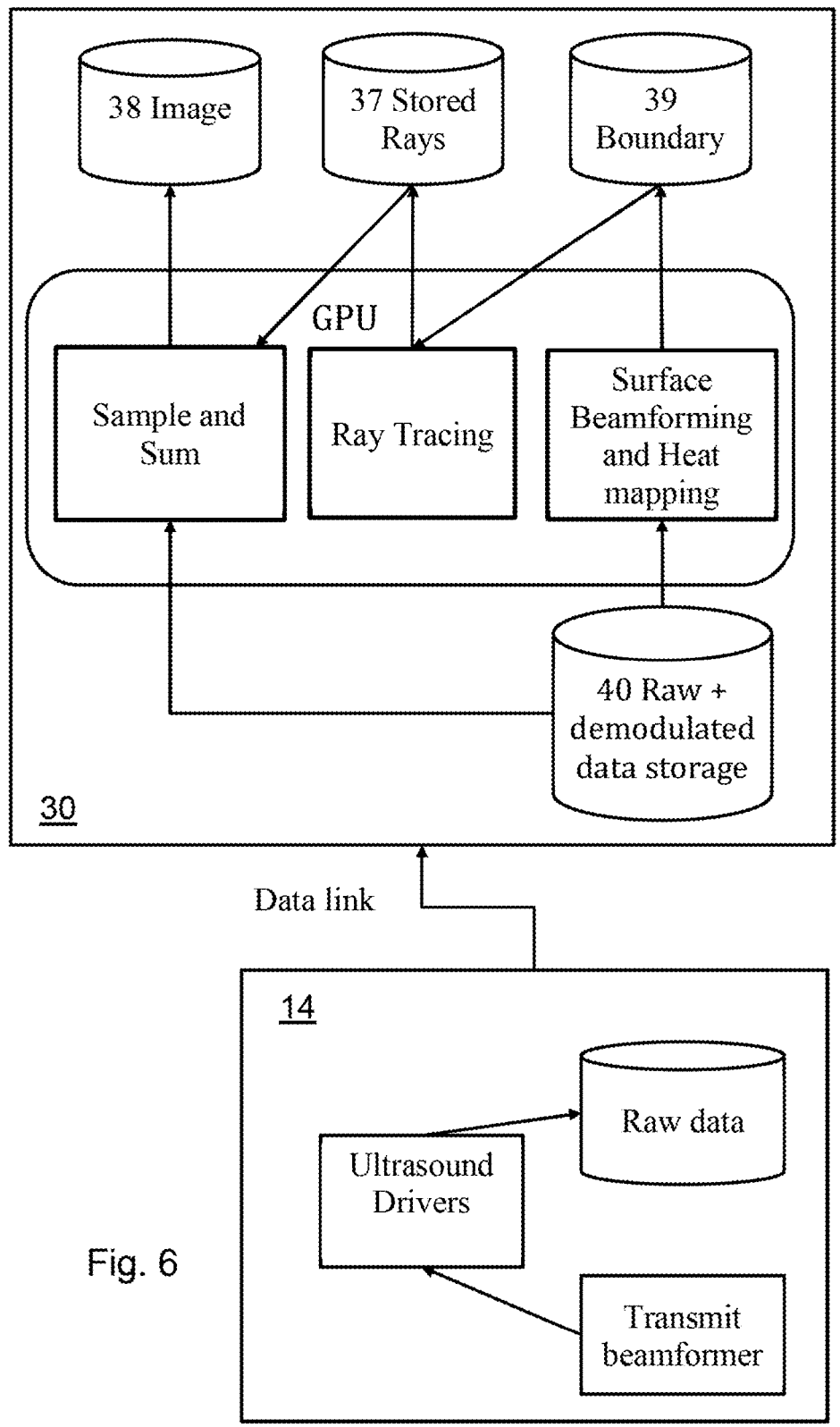
FIG. 6 is a block diagram for processing of ultrasound data.

In preferred embodiments, the imaging device's processing circuit 14 provides ultrasound driving and receiving, signal conditioning, data compression and data storage, while the remote processor 30 performs beamforming and ray tracing. As illustrated by FIG. 6, the ultrasound signals from the tool may be uploaded to storage 40 on a remote computer. A GPU may be used efficiently to beamform the signals; to define the boundary, which is stored in a memory 39; to trace rays, which are stored in memory 37; and to sample and sum the reflection signals in 40 to create the image stored in memory 38.

The ultrasound transducer 12 comprises hundreds of elements, operating together as a phased array for transmission. Phase delays calculated by the tool circuit 14 are sent to drivers to steer the wavefront at the desired angle and shape. The shape generally matches the expected surface shape and there are generally plural steering angles to view the target part or tubular from different perspectives and capture different defects.

For logging tubulars, the transducer 12 may have radially-distributed elements to capture transverse slices of the tubular in each frame. It may be simpler to manufacture and manipulate the transducer as plural transducer segments. The segments are physically separate from each other but combine to capture a 360° slice thru the tubular. The segments may be axially offset from each other to avoid acoustic cross-talk. Each segment images a region of the tubular opposite it and there may be overlap between imaged regions.

The transducer or transducer segments may be divided during transmission and receiving events into apertures comprising a subset of the transducer elements. These apertures need not comprise the same elements or same number of elements. In the example of FIG. 10, a small number of elements on the left of transducer 12 are driver to transmit the wave 11 but a much larger number of elements on the right might be used to receive the expected bulk of the energy, given the inclination with respect to the target 2.

Although the acoustic energy may travel around the tubular to several transducer segments, for the sake of simplicity, the operations of ray tracing may be contained to a single segment, preferably opposite the area of the tubular being processed. FIG. 4 shows an example of one segment transmitting a wavefront 11 at an angle expected to be received by the neighbouring segment. Here the ray would be traced from transmission in the first segment to receiving at the neighbouring segment.

Advantageously, ray tracing in tubular applications is better suited to the realities where transducer standoff distance and transmit angle are affected by the tool twisting around bends and eccentricity. Being able to receive beamform and account for localized defects improves the final image.

The invention claimed is:
1. A method of imaging a tubular comprising:
  a. transmitting a wave towards the tubular using a phased-array ultrasound transducer;
  b. storing received reflection signals reflected off the tubular in a data store;
  c. performing receive beamforming on the reflection signals to locate an inner surface of the tubular;
  d. defining an inner-surface boundary model, using the located inner surface;
  e. tracing rays from the transducer through locations within the tubular and back to the transducer, using the inner-surface boundary model and incorporating localized refractions;
  f. calculating a Time of Flight (ToF) for the rays using a speed of sound (SoS) of a coupling fluid and of the tubular; and
  g. using the ToF, sampling and summing the stored reflection signals to calculate image values for pixels representing the tubular; and
  h. assembling the pixels to visualize the tubular.

2. The method of claim 1, further comprising repeatedly measuring and recording the speed of sound of the coupling fluid; and wherein said calculating the ToF includes using a recorded speed of sound measurement corresponding to a closest location to be visualized.

3. The method of claim 1, further comprising defining an outer-surface boundary model for an outer surface of the tubular, for calculating reflections in the traced rays off the outer surface.

4. The method of claim 1, wherein rays are stored in a memory and then retrieved based on closeness to a given pixel to calculate the image value of the given pixel.

5. The method of claim 4, wherein there are a plurality of rays retrieved for each location in the tubular and at least some of the plurality of rays terminate at multiple transducer elements.

6. The method of claim 1, wherein the reflection signals are stored in Rf or demodulated form.

7. The method of claim 1, wherein the image values are demodulated brightness values.

8. The method of claim 1, further comprising transmitting a plurality of additional waves, each transmitted at a different steering angle and compounding the image values from each of the transmitted waves.

9. The method of claim 8, wherein the inner surface is located in step (c) using a first steering angle normal to the tubular surface and wherein the rays are traced in step (e) from a second steering angle not normal to the tubular surface.

10. The method of claim 1, wherein the wave is transmitted to insonify the inner surface at a constant incidence angle.

11. The method of claim 1, wherein the transmitted wave is characterized by at least one of: being an unfocussed wave; diverging; or having a curved wavefront.

12. The method of claim 1, wherein the inner-surface boundary model is a set of pixel coordinates, or a mathematical equation fit through the located inner surface.

13. The method of claim 1, wherein ultrasound transducer elements used for transmitting the wave are the same or different for receiving the reflection signals.

14. The method of claim 1, transmitting the wave and receiving the reflection signals is performed by separate segments of the ultrasound transducer, each segment imaging a separate region of the tubular.

15. An imaging system for imaging a tubular comprising:
  an imaging tool disposable in the tubular;
  an ultrasound phased-array radially distributed around a body of the tool;
  drive circuits operatively coupled to the array and programmed to transmit a wave;
  a memory for storing received reflection signals from the array; and
  processing circuits programmed to:
    perform receive beamforming on the reflection signals to locate an inner surface of the tubular;
    define an inner-surface boundary model from the located inner surface;
    trace rays from the transducer through locations within the tubular and back to the transducer, using the inner-surface boundary model and incorporating localized refractions;
    calculate a Time of Flight (ToF) for the rays using a speed of sound (SoS) of a coupling fluid and of the tubular; and
    using the ToF, sample and sum the reflection signals to calculate image values for pixels representing the tubular; and
  assemble the pixels to visualize the tubular.

16. The system of claim 15, wherein the phased-array is divided into plural array segments, distributed around the imaging tool.

17. The system of claim 15, wherein the processing circuitry is located remote from the tool and receives the reflection signals from the memory located on the tool.

18. The system of claim 15, further comprising a speed of sound sensor and wherein the memory is arranged to store a speed of sound log from said sensor.

19. The system of claim 15, the processing circuitry further programmed to define a boundary model for an outer surface of the tubular and include reflection off the outer surface in the traced rays.

20. The system of claim 15, wherein the processing circuitry comprises a GPU to trace rays, which are then stored on a datastore and wherein the GPU is arranged to calculate and select one or more closest rays to a given pixel to calculate the pixel's image value.

21. The system of claim 15, wherein the inner surface is located using a first steering angle normal to the tubular surface and wherein the rays are traced from a second steering angle not normal to the tubular surface.

22. The system of claim 15, wherein the boundary model is a set of pixel coordinates, or a mathematical equation fit through the located inner surface.

* * * * *